US012014828B2

(12) United States Patent
Swart et al.

(10) Patent No.: US 12,014,828 B2
(45) Date of Patent: Jun. 18, 2024

(54) USING A SET OF MACHINE LEARNING DIAGNOSTIC MODELS TO DETERMINE A DIAGNOSIS BASED ON A SKIN TONE OF A PATIENT

(71) Applicant: Digital Diagnostics Inc., Coralville, IA (US)

(72) Inventors: Elliot Swart, Phoenix, AZ (US); Elektra Efstratiou Alivisatos, Cambridge, MA (US); Joseph Ferrante, Cambridge, MA (US); Elizabeth Asai, Boston, MA (US)

(73) Assignee: Digital Diagnostics Inc., Coralville, IA (US)

( * ) Notice: Subject to any disclaimer, the term of this patent is extended or adjusted under 35 U.S.C. 154(b) by 393 days.

(21) Appl. No.: 17/619,173

(22) PCT Filed: Jun. 15, 2020

(86) PCT No.: PCT/US2020/037765
§ 371 (c)(1),
(2) Date: Dec. 14, 2021

(87) PCT Pub. No.: WO2020/257108
PCT Pub. Date: Dec. 24, 2020

(65) Prior Publication Data
US 2022/0309668 A1 Sep. 29, 2022

Related U.S. Application Data

(60) Provisional application No. 62/862,844, filed on Jun. 18, 2019.

(51) Int. Cl.
*G06T 7/90* (2017.01)
*A61B 5/00* (2006.01)
(Continued)

(52) U.S. Cl.
CPC ............ *G16H 50/20* (2018.01); *A61B 5/1032* (2013.01); *A61B 5/441* (2013.01); *A61B 5/7267* (2013.01);
(Continued)

(58) Field of Classification Search
CPC ......... G16H 50/20; G06T 7/90; G06T 7/0014; G06T 2207/10024; G06T 2207/20076;
(Continued)

(56) References Cited

U.S. PATENT DOCUMENTS

| 6,690,822 B1 | 2/2004 | Chen et al. |
| 8,296,247 B2 | 10/2012 | Zhang et al. |

(Continued)

FOREIGN PATENT DOCUMENTS

| CA | 2479456 C | 7/2012 |
| CA | 2907733 A1 | 9/2014 |

(Continued)

OTHER PUBLICATIONS

AAD. "Skin Cancer." American Academy of Dermatology Association, Last Updated: Jun. 1, 2021, 7 pages, [Online] [Retrieved Feb. 3, 2022], Retrieved from the Internet <URL:https://www.aad.org/media/stats-skin-cancer>.

(Continued)

*Primary Examiner* — Syed Haider
(74) *Attorney, Agent, or Firm* — Fenwick & West LLP

(57) ABSTRACT

Systems and methods are disclosed herein for determining a diagnosis based on a base skin tone of a patient. In an embodiment, the system receives a base skin tone image of a patient, generates a calibrated base skin tone image by calibrating the base skin tone image using a reference calibration profile, and determines a base skin tone of the patient based on the calibrated base skin tone image. The system receives a concern image of a portion of the patient's (Continued)

skin, and selects a set of machine learning diagnostic models from a plurality of sets of candidate machine learning diagnostic models based on the base skin tone of the patient, each of the sets of candidate machine learning diagnostic models trained to receive the concern image and output a diagnosis of a condition of the patient.

17 Claims, 6 Drawing Sheets

(51) Int. Cl.
    *A61B 5/103*     (2006.01)
    *G06T 7/00*     (2017.01)
    *G06V 10/56*     (2022.01)
    *G06V 10/72*     (2022.01)
    *G06V 10/764*     (2022.01)
    *G06V 40/10*     (2022.01)
    *G16H 50/20*     (2018.01)

(52) U.S. Cl.
    CPC .......... *A61B 5/7275* (2013.01); *G06T 7/0014* (2013.01); *G06T 7/90* (2017.01); *G06V 10/56* (2022.01); *G06V 10/72* (2022.01); *G06V 10/764* (2022.01); *G06V 40/10* (2022.01); *A61B 2576/02* (2013.01); *G06T 2207/10024* (2013.01); *G06T 2207/20076* (2013.01); *G06T 2207/20081* (2013.01); *G06T 2207/20084* (2013.01); *G06T 2207/30088* (2013.01); *G06T 2207/30168* (2013.01); *G06V 2201/03* (2022.01)

(58) Field of Classification Search
    CPC . G06T 2207/20081; G06T 2207/20084; G06T 2207/30088; G06T 2207/30168; G06V 10/56; G06V 40/10; G06V 10/72; G06V 10/764; G06V 2201/103; A61B 5/1032; A61B 5/441; A61B 5/7267; A61B 5/7275; A61B 2576/02
    See application file for complete search history.

(56) References Cited

U.S. PATENT DOCUMENTS

| | | | |
|---|---|---|---|
| 8,583,216 B2 | 11/2013 | Pershing et al. | |
| 8,675,960 B2 | 3/2014 | Reid et al. | |
| 10,130,297 B2 | 11/2018 | Schnidar et al. | |
| 2007/0016076 A1 | 1/2007 | Youabian | |
| 2010/0185064 A1 | 7/2010 | Bandic et al. | |
| 2012/0008838 A1* | 1/2012 | Guyon | G16H 50/20 382/128 |
| 2013/0279802 A1 | 10/2013 | Van Der Merwe | |
| 2015/0254851 A1* | 9/2015 | Daly | G06T 5/73 382/128 |
| 2016/0166194 A1* | 6/2016 | Gareau | A61B 5/14552 600/328 |
| 2018/0061046 A1* | 3/2018 | Bozorgtabar | G06T 7/11 |
| 2018/0068426 A1 | 3/2018 | Matsunaga | |
| 2018/0204111 A1 | 7/2018 | Zadeh et al. | |
| 2019/0340762 A1* | 11/2019 | Lapiere | G06T 7/0014 |
| 2020/0327670 A1* | 10/2020 | Connor | G06T 19/006 |

FOREIGN PATENT DOCUMENTS

| | | |
|---|---|---|
| DE | 602004025535 | 3/2005 |
| WO | WO 2011/063032 A1 | 5/2011 |
| WO | WO 2014/172033 A1 | 10/2014 |
| WO | WO 2018/101572 A1 | 6/2018 |
| WO | WO 2020/257108 A1 | 12/2020 |

OTHER PUBLICATIONS

ASA. "Race and Ethnicity." American Sociological Association, 2 pages, n.d., [Online] [Retrieved Feb. 3, 2022], Retrieved from the Internet <URL:https://www.asanet.org/topics/race-and-ethnicity>.

Chan, I. L. et al. "Characteristics and Management of Asian Skin." International Journal of Dermatology, vol. 58, No. 2, Feb. 2019, pp. 131-143.

Coley, M. K. et al. "Managing Common Dermatoses in Skin of Color." Seminars in Cutaneous Medicine and Surgery, vol. 28, No. 2, Jun. 2009, pp. 63-70.

D'Orazio, J. et al. "UV Radiation and the Skin." International Journal of Molecular Sciences, vol. 14, No. 6, Jun. 2013, pp. 12222-12248.

Del Bino, S. et al. "Clinical and Biological Characterization of Skin Pigmentation Diversity and its Consequences on UV Impact." International Journal of Molecular Sciences, vol. 19, No. 9, Sep. 2018, pp. 1-44.

Fitzpatrick, T. B. "The Validity and Practicality of Sun-Reactive Skin Types I Through VI." Archives of Dermatology, vol. 124, No. 6, Jun. 1988, pp. 869-871.

Haenssle, H. A. et al. "Man Against Machine: Diagnostic Performance of a Deep Learning Convolutional Neural Network for Dermoscopic Melanoma Recognition in Comparison to 58 Dermatologists." Annals of Oncology, vol. 29, No. 8, Aug. 2018, pp. 1836-1842.

Ho, B. K. et al. "Color Bar Tool for Skin Type Self-Identification: A Cross-Sectional Study." Journal of the American Academy of Dermatology, vol. 73, No. 2, Aug. 1, 2015, pp. 312-313E1.

Kundu, R. V. et al. "Dermatologic Conditions in Skin of Color: Part I. Special Considerations for Common Skin Disorders." American Family Physician, vol. 87, No. 12, Jun. 15, 2013, pp. 850-856.

Kundu, R. V. et al. "Dermatologic Conditions in Skin of Color: Part II. Disorders Occurring Predominantly in Skin of Color." American Family Physician, vol. 87, No. 12, Jun. 15, 2013, pp. 859-865.

Lashbrook, A. "AI-Driven Dermatology Could Leave Dark-Skinned Patients Behind." The Atlantic, Aug. 16, 2018, 5 pages, [Online] [Retrieved Feb. 3, 2022], Retrieved from the Internet <URL:https://www.theatlantic.com/health/archive/2018/08/machine-learning-dermatology-skin-color/567619/>.

Vespa, J. et al. "Demographic Turning Points for the United States: Population Projections for 2020 to 2060." United States Census, Current Population Reports, Mar. 2018, pp. 1-15.

PCT International Search Report and Written Opinion, International Application No. PCT/US2020/037765, dated Sep. 4, 2020, 14 Pages.

Extended European Search Report and Written Opinion, European Patent Application No. 20825716.2, Jun. 28, 2023, 7 pages.

Patnaik, S.K. et al. "Automated Skin Disease Identification Using Deep Learning Algorithm," *Biomedical & Pharmacology Journal*, vol. 11, No. 3, Sep. 2018, pp. 1429-1436.

\* cited by examiner

USING A SET OF MACHINE LEARNING DIAGNOSTIC MODELS TO DETERMINE A DIAGNOSIS BASED ON A SKIN TONE OF A PATIENT

CROSS REFERENCE TO RELATED APPLICATIONS

This application is a national phase of International Application No. PCT/US2020/037765, titled "Using a Set of Machine Learning Diagnostic Models to Determine a Diagnosis Based on a Skin Tone of a Patient", filed on Jun. 15, 2020, which claims the benefit of U.S. Provisional Application No. 62/862,844 filed on Jun. 18, 2019, the contents of both of which are hereby incorporated by reference herein in its entirety.

BACKGROUND

Skin pigmentation, also referred to herein as skin tone or skin color, is highly variable across and within populations. Skin color is important from a clinical perspective because the incidence, morbidity, clinical presentation, and treatment of skin diseases may vary based on skin type. However, biases against non-white skin types in dermatology practice and research today are having a significant impact on quality of care. Presentation of skin diseases may vary by skin tone, with significant impacts on survival rate. As an example, skin cancers such as melanoma, the deadliest form of skin cancer, are diagnosed at later, less-treatable stages, in people of color (i.e., non-white), due in part to their presentation in non-UV exposed areas of the body, such as the hands, nails, feet, and mucous membranes, which are not commonly examined. Therefore, while there is a higher incidence of melanoma in Caucasians, there is a higher mortality rate among skin of color.

One of the most well-known classification systems is the Fitzpatrick scale, which categorizes skin color into six skin types (I-VI) based on self-reported questionnaires. Skin Types I-IV were originally created in 1975 in France to categorize Caucasian skin based on a clinical response to ultraviolet (UV) radiation, but Type V (brown Asian and Latin American) and Type VI (dark African skin) were only later added to capture non-Caucasian skin tones based on constitutive pigmentation or ethnic origin. The Fitzpatrick scale is commonly used in skin cancer studies; however, critiques of the tool note errors associated with self-reporting and the limited applicability to all skin types given the basis of ethnic origin, which is changing, resulting in difficulties with the clustering of certain ethnic/racial group into one skin type.

Use of systems like the Fitzpatrick scale are inadequate in terms of their ability to accurately define skin color. This in turn results in imprecise or missed diagnoses of skin conditions through existing processes.

SUMMARY

The present disclosure relates to an automated system and method for objectively analyzing and classifying skin tones using machine learning. Such analysis and classification may be used to augment the analysis, diagnosis, and treatment of skin. In an embodiment, the system receives a base skin tone image of a patient. The system generates a calibrated base skin tone image by calibrating the base skin tone image using a reference calibration profile. The system determines a base skin tone of the patient based on the calibrated base skin tone image. The system may then receive a concern image of a portion of the patient's skin, and may select a set of machine learning diagnostic models from a plurality of sets of candidate machine learning diagnostic models based on the skin tone measurement of the patient, where each of the sets of candidate machine learning diagnostic models may be trained to receive the concern image and output a diagnosis of a condition of the patient.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION (a) Environment Overview

Figure 1:
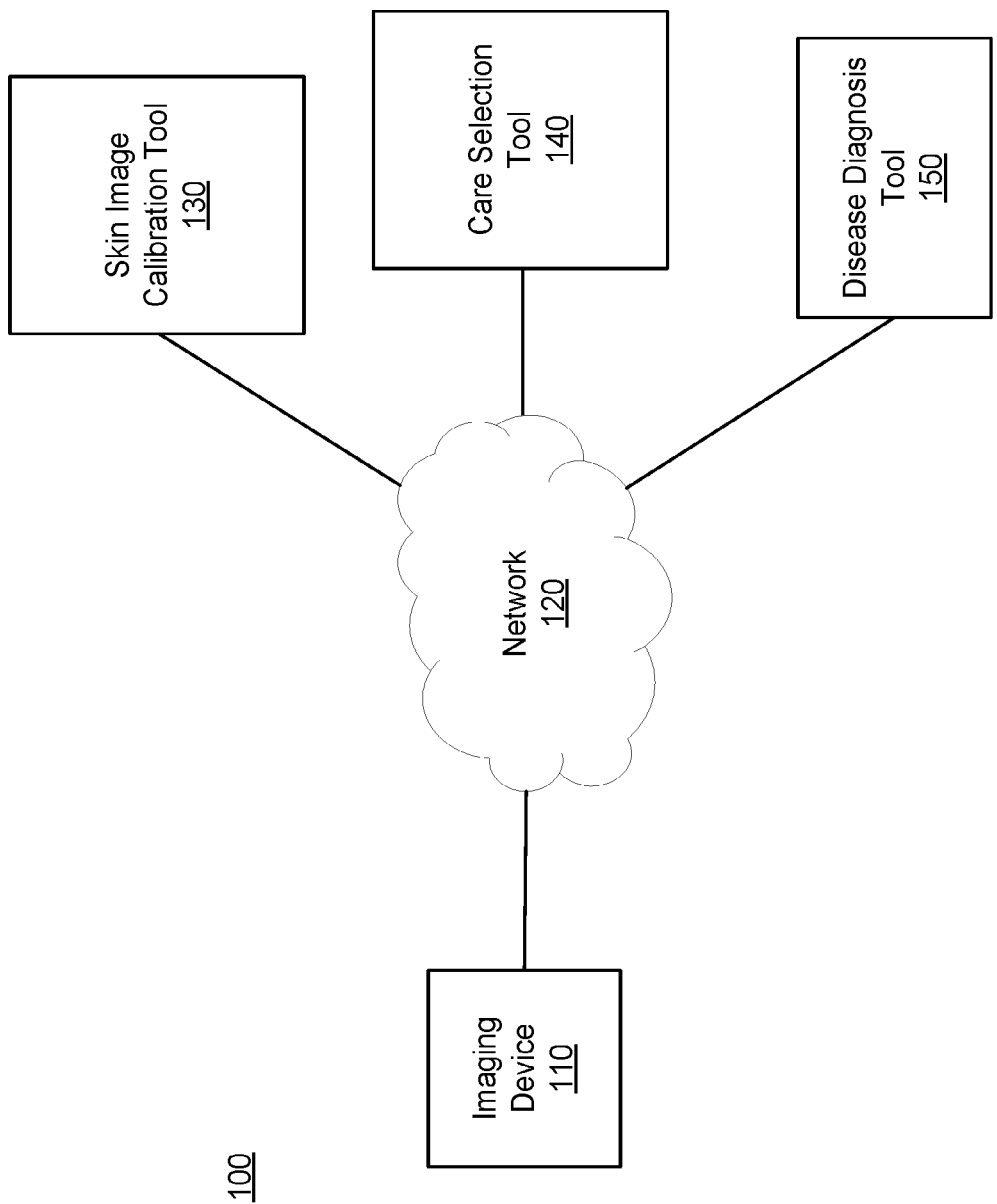
FIG. 1 is an exemplary block diagram of system components in an environment for utilizing a skin image calibration tool, in accordance with one embodiment.

FIG. 1 is an exemplary block diagram of system components in an environment for utilizing a skin image calibration tool, in accordance with one embodiment. Environment 100 includes imaging device 110, network 120, skin image calibration tool 130, care selection tool 140, and disease diagnosis tool 150. Imaging device 110 may be any device configured to capture an image of an affected area of a patient. An example that pervades this disclosure is skin image calibration and skin disease diagnosis; however, the imaging, calibration, and diagnosis aspects disclosed herein may apply to any other organ of the human body (e.g., the retina). Imaging device 110 may be specially configured to capture images of a patient's skin. Alternatively, imaging device 110 may be a generic client device, such as a smartphone, laptop, tablet, or other camera-equipped computing device, with software (e.g., an application) installed thereon for processing the image in the manners disclosed herein. In an embodiment, imaging device 110 may be a generic client device that captures images and transmits the images to a remote server (e.g., skin image calibration tool 130), where processing and calibration of the image is performed by the remote server.

Network 120 may be any communications network, such as a local area network, a wide area network, the Internet, and the like. Alternatively, or additionally, network 120 may represent on-device activity (such as in a scenario where some or all functionality of skin image calibration tool 130, care selection tool 140, and/or disease diagnosis tool 150, were installed on-board imaging device 110).

Skin image calibration tool 130 receives a base skin tone image of a patient, and determines a base skin tone of the patient from the base skin tone image. The term base skin tone image, as used here, in may refer to an image captured that satisfies certain criteria, or was captured based on instructions that the image should satisfy certain criteria. For example, a base skin tone image, in an embodiment, is an image that should show healthy, untanned skin. The term base skin tone, as used herein, may refer to a value representative of a pigmentation (or tone, as interchangeably used herein) of a patient's skin. Further details on the mechanics of how skin image calibration tool 130 determines the base skin tone are described in further detail below with respect to FIGS. 2-6. While depicted as being opposite network 120 in FIG. 1, skin image calibration tool 130 may, in part or in whole, be installed on imaging device 110, and/or in a device local to imaging device 110.

Care selection tool 140 receives input (e.g., a determined base skin tone), and outputs a care decision. For example, based on a base skin tone determined by skin image calibration tool 130, care selection tool 140 may select a machine learning model that is best optimized for diagnosing a concern image. Disease diagnosis tool 150 performs a diagnosis based on its inputs. For example, disease diagnosis tool 150 may take a concern image as input, and may output a diagnosis. Further details of how care selection tool 140 and disease diagnosis tool 150 perform these and other operations is disclosed in further detail below with respect to FIGS. 3-6. Wherever a classifier or machine learning diagnostic model is mentioned herein, the performance of inputting data into such a model and obtaining output from the model may be performed by disease diagnosis tool 150. Like skin image calibration tool 130, while depicted as being opposite network 120 in FIG. 1 from each other element depicted in FIG. 1, care selection tool 140 and/or disease diagnosis tool 150 may be, in part or in whole, installed on imaging device 110 and/or in a device local to imaging device 110. Functionality of skin image calibration tool 130, care selection tool 140, and disease diagnosis tool 150, may be consolidated on a single server or group of servers, and/or may be distributed across many servers.

Figure 2:
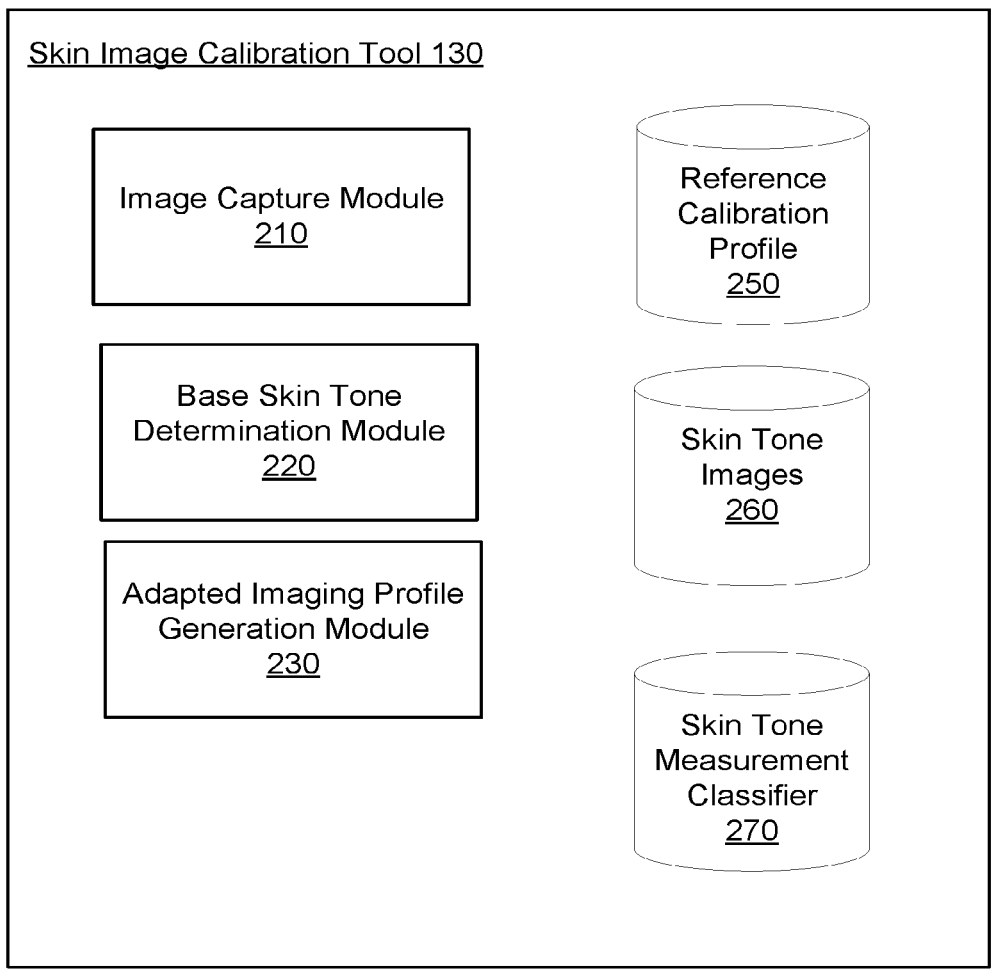
FIG. 2 is an exemplary block diagram of modules and components of a skin image calibration tool, in accordance with one embodiment.

FIG. 2 is an exemplary block diagram of modules and components of a skin image calibration tool, in accordance with one embodiment. As depicted in FIG. 2, skin image calibration tool 130 includes various modules, such as image capture module 210, base skin tone determination module 220, and adapted imaging profile generation module 230. Skin image calibration tool 130 is also depicted as including various databases, such as reference calibration profile 250, skin tone images 260, and base skin tone classifier 270. The modules and databases depicted are merely exemplary, and more or fewer modules and/or databases may be used to achieve the functionality disclosed herein.

Image capture module 210 captures a base skin tone image of a patient's skin for further processing. In order to capture the image, image capture module 210 first acquires image data from a camera of imaging device 110. The acquired image data may be completely uncalibrated and thus not yet be synthesized into an image perceptible by a human being. This RAW image data often effectively represents photon intensity received per pixel in the bayer pattern requires further post processing, such as debayering and color correction in order to be converted into a calibrated image. Image capture module 210 may apply a reference calibration profile (e.g., as retrieved from reference calibration profile 250, or from memory of imaging device 110) to the acquired image data in order to capture the base skin tone image. Imaging device 110 may be calibrated to be within set tolerances, including but not limited to, colorimetric accuracy (conventionally described in terms of Delta E, measuring change in visual perception of two given colors) and optical properties, such as relative lens positions. This calibration may be implemented in any number of ways, including, for example, camera settings (such as exposure or channel gains), color transformation profiles (such as ICC profiles) and/or transformations based on spatially relevant points (such as which pixels are located within the camera's effective field of view). These calibrations may be performed by the factory when creating imaging device 110, and/or may be instructed by imaging device 110. The resulting calibration of imaging device 110 forms the reference calibration profile.

In an embodiment, image capture module 210, prior to acquiring image data, may cause an output of instructions to be provided (e.g., displayed and/or audio instructions) to an operator of imaging device 110. The operator may be any human being, such as a medical assistant, a minimally-trained operator, or the patient. The instructions may include instructions to take a photograph of skin having one or more pre-defined characteristics, such as the skin being on the inner-wrist, the skin being healthy, the skin being untanned, the skin being a consistent tone without any artifacts, such as a mole, being present, and so on. Image capture module 210 may perform processing on the base skin tone image to verify whether the skin photographed complies with the pre-defined characteristics and whether the image itself is of sufficient quality. For example, pattern recognition may be performed, or the base skin tone image may be input into a classifier that is trained to output a label of whether the base skin tone image is compliant with the instructions.

Image capture module 210 may capture a plurality of base skin tone images. Image capture module 210 may prompt the operator to capture several base skin tone images. For example, a patient may not have uniform skin tone across the patient's body, and therefore, multiple skin tone images may be used to obtain a more robust data set for determining the base skin tone of the patient. Image capture module 210 may store base skin tone images in skin tone images database 260. Skin tone image database 260 may store base skin tone images in association with an electronic health record of a patient that includes other information about the patient, including biographic information, demographic information, and any other information describing the patient.

Base skin tone determination module 220 determines a base skin tone for a patient based on one or more base skin tone images. Base skin tone determination module 220 may determine the base skin tone in any of a variety of manners. In an embodiment, base skin tone determination module 220 may determine a numerical representation of each pixel of the calibrated base skin tone image. For example, each color of each pixel may correspond to a number on a scale. Base skin tone determination module 220 may generate an aggregate representation by performing a statistical operation based on each numerical representation. For example, base skin tone determination module 220 may average the numerical representation. Where multiple base skin tone images are used, base skin tone determination module 220 may repeat this activity for each base skin tone image, and then perform a statistical operation on each of the aggregate representations, resulting in an aggregate representation of the entire set of base skin tone images. Base skin tone determination module 220 may then map, using the scale, the aggregate representation to a point in a color space, and may assign this point as the base skin tone. Alternatively, rather than immediately assigning this point as the base skin tone, base skin tone determination module 220 may map the point in color space into a discrete value in a classification system, such as the Fitzpatrick system, or any other classification system. This embodiment of base skin tone determination may be sufficient in many cases, but it may not account for pigmentation inconsistencies within the reference area, such as hypopigmented or hyperpigmented skin patches, so other measurement means may be performed.

In an embodiment, base skin tone determination module 220 may input the base skin tone image(s) into base skin tone classifier 270. Base skin tone classifier 270 may be a machine learning model that is trained to generate a discrete value from a set of images. For example, in order to train base skin tone classifier 270, expert graders may assign a value to each image in a training set. The labels may indicate a precise skin tone of a patient. In an embodiment, the labels may additionally, or alternatively, indicate an attribute of the skin tone (e.g., that the skin is hypopigmented or hyperpigmented). Thus, base skin tone classifier 270 may output the base skin tone of the patient.

Alternatively, or additionally, base skin tone classifier 270 may output a type of skin indicated (e.g., hypopigmented or hyperpigmented skin, or normal skin). Base skin tone determination module 220 may determine, based on the output of base skin tone classifier 270, that the aforementioned aggregate representation method is sufficient responsive to receiving output from the classifier that skin is normal. Responsive to receiving output from the classifier that the skin is of a certain type (e.g., hypopigmented or hyperpigmented), base skin tone determination module 220 may determine to use a measurement output by base skin tone classifier 270 as the base skin tone. Example classifier algorithms for base skin tone classifier 270 may include convolutional neural networks, support vector machines on extracted features, and XGBoost on extracted features. As another example, a segmentation algorithm could be trained to separate healthy, untanned skin from discolored skin, and then either the basic approaches described above, or a different classifier could be used solely on the healthy patches of skin to determine the base skin tone. Example segmentation algorithms include fully convolutional neural networks, Otsu method, and thresholding the color variance.

Adapted imaging profile generation module 230 generates an adapted imaging profile. The term adapted imaging profile, as used herein, may refer to imaging parameters that are optimized to acquire a skin concern image that is most useful for diagnosis, relative to a skin concern image that would be acquired using the reference calibration profile alone. Adapted imaging profile generation module 230 may generate the adapted imaging profile in a number of ways. In an embodiment, adapted imaging profile generation module 230 may determine, based on a data structure such as a mapping table, a set of predefined imaging parameters stored in reference calibration profile database 250 as mapping to the determined base skin tone. In another embodiment, instead of basing the imaging parameters on a data structure such as a mapping table, the adapted imaging profile generation module 230 would use the base skin tone to adjust the imaging parameters as a difference from base values using the numerical representation of skin tone. An example of this could include increasing the exposure proportional to the darkness of the patients skin to maximize detail. A more complex example could involve interpolating between the values of known profiles to choose intermediate values for skin tones that fall between the range of two explicitly listed profiles. Adapted imaging profile generation module 230 may store the adapted imaging profile in reference calibration profile database 250.

Figure 3:
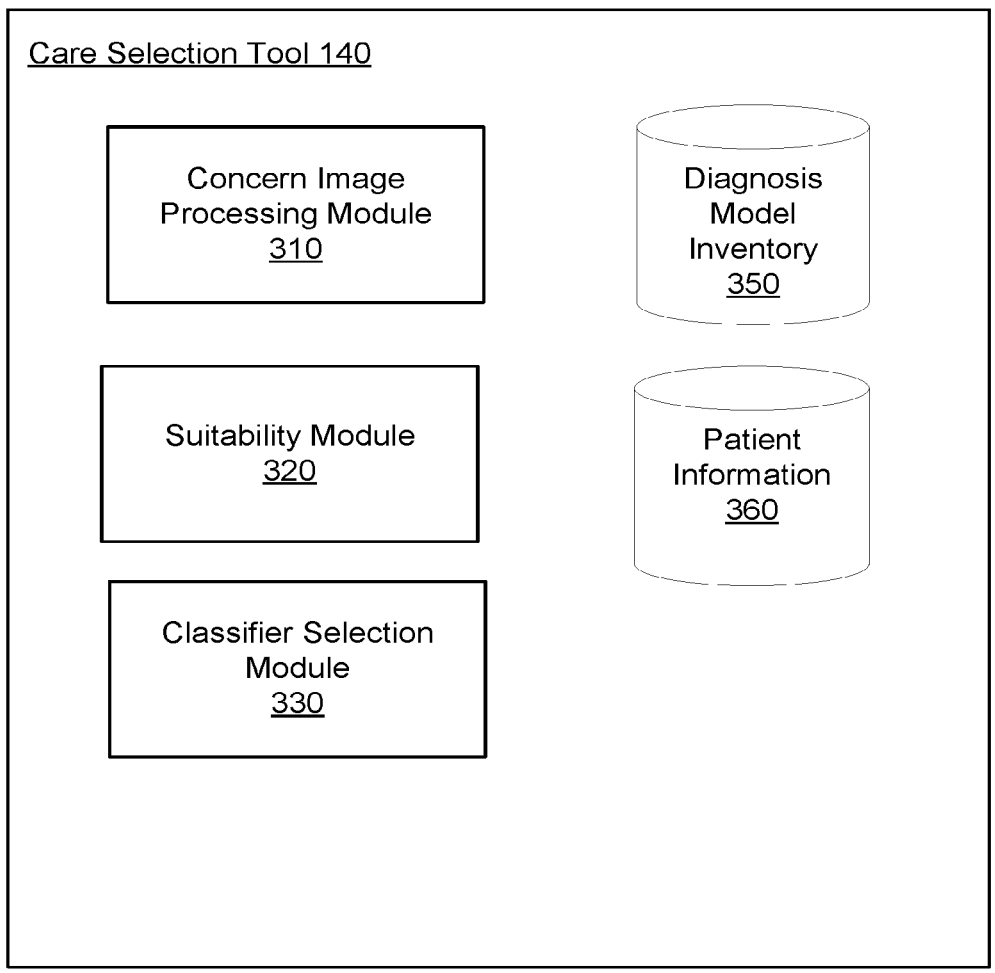
FIG. 3 is an exemplary block diagram of modules and components of a care selection tool, in accordance with one embodiment.

FIG. 3 is an exemplary block diagram of modules and components of a care selection tool, in accordance with one embodiment. As depicted in FIG. 3, care selection tool 140 includes various modules, such as concern image processing module 310, suitability module 320 and classifier selection module 330. Care selection tool 140 also includes various databases, such as diagnosis model inventory 350 and patient information 360. The modules and databases depicted with respect to FIG. 3 are merely exemplary; fewer or more modules and/or databases may be used to achieve the functionality of care selection tool 140 described herein.

Concern image processing module 310 receives a skin concern image and may calibrate the skin concern image using the adapted imaging profile. Calibration of the skin concern image occurs in the same manner as calibration of the base skin tone image, except that the adapted imaging profile is used instead of the reference calibration profile.

Suitability module 320 determines whether the skin concern image is suitable for diagnosis. Suitability may be based on any predefined criteria. For example, a regulatory agency may indicate that some classifications (e.g., Fitzpatrick system classifications 1-3) are suitable for diagnosis using the systems and methods disclosed herein, but other classifications are not suitable for diagnosis using the systems and methods disclosed herein (e.g., darker skin tones may experience a higher error rate in diagnosing whether a mole is benign). As another example, the skin concern image may fail a quality parameter that must be met for processing (e.g. the skin concern image is over-exposed, under-exposed, does not show enough of the affected skin area, or any other predefined parameter). Additional example validity criteria include no color channel saturation across the image (a channel being at maximum value and thus not being able to provide an accurate measurement would indicate failure), or passing a machine learning based quality checker. Image quality issues can be screened using a convolutional neural network classifier trained on examples of images with sufficient quality and images with insufficient quality. Additionally, image quality issues can be screened for using features extracted from the image, these features may include measures of the high frequency content of the images, and a histogram of the colors.

Responsive to determining that the skin concern image is not suitable for diagnosis, suitability module 320 may cause a prompt to be output to the operator indicating that the skin concern image is not suitable for diagnosis. In an embodiment where the skin concern image is not suitable for diagnosis due to a quality issue, suitability module 320 may prompt the operator to capture another skin concern image satisfying the quality parameter. Where the recaptured image is taken, in an embodiment, suitability module 320 may instruct that the reference calibration profile be used to generate the recaptured skin concern image. In such an embodiment, where the recaptured image still does not satisfy a quality parameter, suitability module 320 may prompt the operator to manually check the images for errors, to manually check for signs of a camera malfunction, to yet again re-take the skin concern image, and/or to re-take the base skin tone image (which may trigger re-generation of the adapted imaging profile using the retaken base skin tone image, where the re-generated adapted imaging profile may be used to calibrate further skin concern images for the patient). In an embodiment where the skin concern image is not suitable due to a characteristic of the patient, suitability module 320 may prompt the operator to instruct the patient that a diagnosis cannot be completed. Additional information may be prompted to the operator as well (e.g., instructions for the patient to obtain diagnosis by a medical doctor).

Classifier selection module 330 selects one or more classifiers, such as a set of machine learning diagnostic models, based on the base skin tone of the patient, the selected classifier to be used to establish care of the patient. The set may include one or more machine learning models and may additionally include heuristics that, together, form a workflow for care of the patient. A plurality of classifiers may be stored in diagnosis model inventory 350. Each of these classifiers may be associated with criteria that, if satisfied, indicate to classifier selection module 330 that the classifier is to be used for diagnosis of the patient. Classifier selection module 330 may select a classifier based on information additional to the base skin tone, the additional information being retrieved from patient information database 360. The additional information may include any information of the patient's electronic patient record, such as biographical information, demographic information, and/or any other information descriptive of the patient.

In an embodiment, classifier selection module 330 may perform activity beyond selecting one or more particular classifiers, or may perform activity in connection with obtaining further inputs for particular classifiers. For example, classifier selection module 330 may determine that the base skin tone is a high-risk skin tone (e.g., as is indicated in a database that maps base skin tones to risk categories). For example, the base skin tone may correspond to a very light skinned person who has higher incidences of skin cancer. Responsively, classifier selection module 330 may prompt inputs of answers to questions that are relevant to informing care (e.g., the patient may be prompted to answer questions about the patient's sun exposure behavior). As another example, classifier selection module 330 may prompt that further skin concern images be captured (e.g., palms of the hands and soles of the feet where the patient has darker skin tones that cause those patients to be more prone to dangerous growths in those locations).

In an embodiment, classifier selection module 330 may have a number of classifiers available in diagnosis model inventory 350, each of the available classifiers corresponding to a different range of skin tones. Classifier selection module 330 may select a classifier based on the base skin tone of the patient. The selected classifier may be trained to be optimized for its corresponding range of skin tones, and may be less effective or ineffective where a patient has a base skin tone outside of that range. The selected classifier may take the concern image as input, with or without other information such as the base skin tone and/or additional patient information, and may output a diagnosis.

In an embodiment, classifier selection module 330 is not used as a gatekeeper to select a classifier. Instead, care selection tool 140 inputs the base skin tone and the concern image into the classifier (possibly with additional patient information), and outputs a diagnosis. As another example embodiment in this vein, a classifier may be used that takes the skin concern image as input, and outputs probabilities of a diagnosis. Care selection tool 140 then weights the probabilities based on the base skin tone of the patient.

Where a classifier outputs a diagnosis, the diagnosis may be a direct diagnosis (e.g., the concern image indicates that no disease is present, or a particular identification of a disease that is present). The diagnosis may, alternatively, be a plurality of probabilities, each probability corresponding to a different candidate diagnosis, the probability indicating the likelihood that the disease corresponds to each candidate diagnosis. Classifier selection module 330 may output the probabilities directly to the operator. In an embodiment, classifier selection module 330 may cause the candidate diagnosis with the highest probability to be displayed to the operator. Classifier selection module 330 may compare each probability to a threshold, and may limit candidate diagnoses displayed to the operator to those candidate diagnoses whose corresponding probabilities exceed the threshold. Each different candidate diagnosis may have a different corresponding threshold that must be crossed for the candidate diagnosis to be displayed to the operator.

Care selection tool 140 may determine, based on two or more candidate diagnoses having a probability that exceeds a threshold being output by a classifier, that at least two diseases cannot be ruled out as being depicted by the skin concern image. Accordingly, care selection tool 140 may prompt the operator to instruct the patient to obtain an expert opinion (e.g., from a medical doctor). Care selection tool 140 may withhold the two or more candidate diagnoses, or may cause the two or more candidate diagnoses to be indicated.

While skin is a primary example, care selection tool 140 may apply care selection based on any patient attributes. In an embodiment, a model may be trained to classify a patient based on any condition (e.g., skin tone, weight, gender, jaundice, diabetes, and/or any other condition of the patient). Care selection tool 140 may determine, based on output of the model, further models to be used to determine care for the patient (e.g., a precise model trained to determine whether a skin condition associated with diabetes is present in the patient).

In an embodiment, care selection tool 140 may receive biometric data corresponding to a patient. The biometric data may include a visual image such as the images discussed herein and any other type of image (whether using a camera lens or a spectrum that captures internal organs, such as a sonogram), and may be an image in non-visible wavelengths (e.g., infrared, ultraviolet, x-ray, and so on). The biometric data may be any other data about the patient, or a combination of different types of data. Exemplary biometric data includes measurements derived from bloodwork, cardiac activity (e.g., as measured by an electrocardiogram), pulse data, and any other data describing biometric activity of the patient. Care selection tool 140 may input the biometric data into a classifier trained to obtain an attribute of the patient. For example, bloodwork data may be input into the classifier, and the classifier may output whether the bloodwork indicates the patient has one or more conditions, such as a disease (e.g., diabetes).

Care selection tool 140 may select a set of machine learning models from a plurality of sets of candidate machine learning diagnostic models based on the attribute of the patient, where each of the sets of candidate machine learning diagnostic models are trained to receive the attribute and output a diagnosis of a condition of the patient. For example, a set of machine learning models corresponding to a particular disease, such as diabetes, might include machine learning models that take, in addition to the disease itself, other inputs (e.g., retinal images, images of toes) to obtain outputs relating to the disease (e.g., determination of whether the patient has diabetic retinopathy based on a retinal image, determination of whether the patient has a toe condition associated with diabetes, and so on). The operator might be prompted to obtain additional information about the patient, or to instruct the patient to obtain the other inputs, by visiting other operators (e.g., medical doctors) to determine additional information that might inform the selected set of machine learning models.

Figure 4:
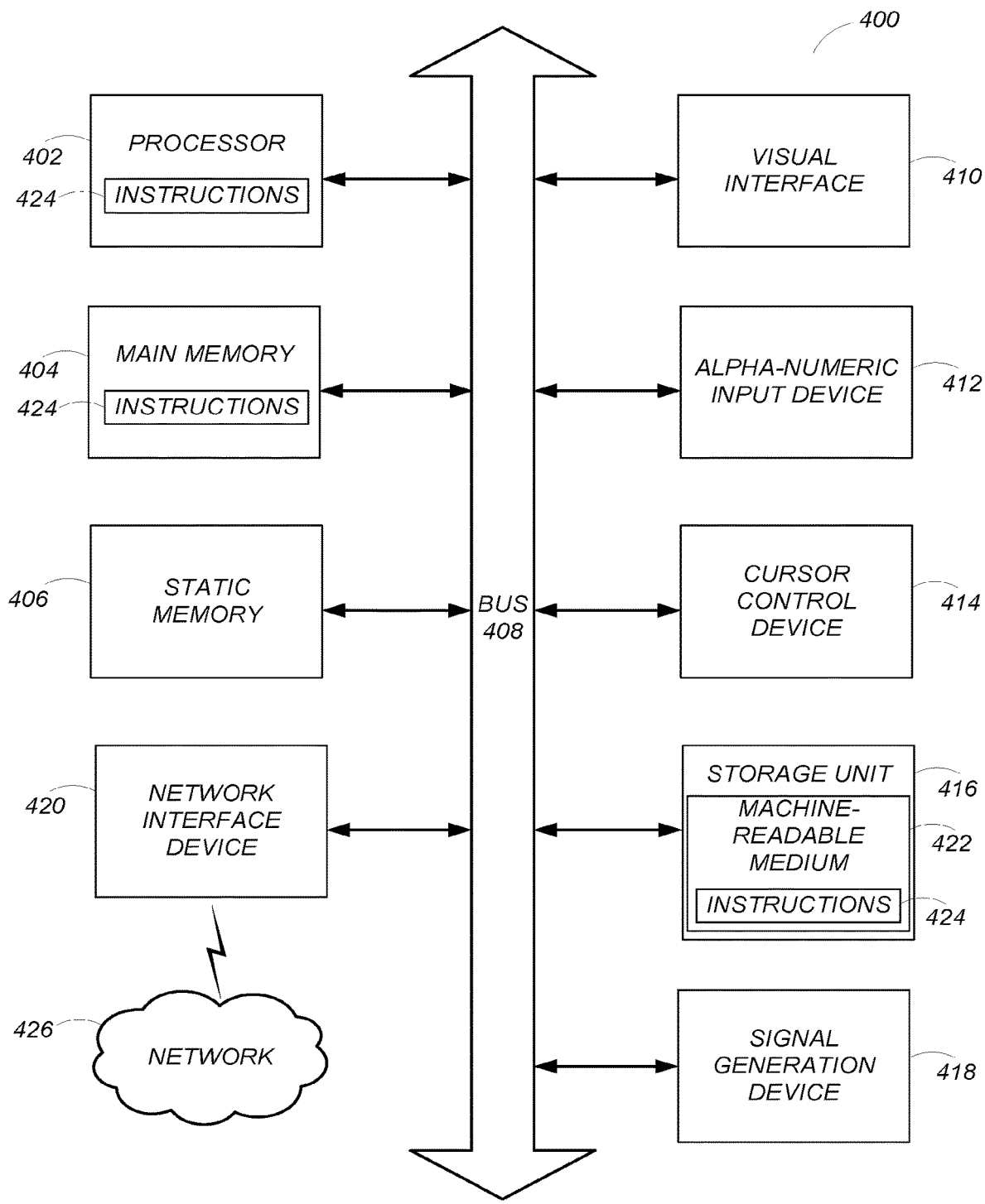
FIG. 4 is a block diagram illustrating components of an example machine able to read instructions from a machine-readable medium and execute them in a processor (or controller).

FIG. 4 is a block diagram illustrating components of an example machine able to read instructions from a machine-readable medium and execute them in a processor (or controller). Specifically, FIG. 4 shows a diagrammatic representation of a machine in the example form of a computer system 400 within which program code (e.g., software) for causing the machine to perform any one or more of the methodologies discussed herein may be executed. The program code may be comprised of instructions 424 executable by one or more processors 402. In alternative embodiments, the machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a personal digital assistant (PDA), a cellular telephone, a smartphone, a web appliance, a network router, switch or bridge, or any machine capable of executing instructions 424 (sequential or otherwise) that specify actions to be taken by that machine. Further, while only a single machine is illustrated, the term "machine" shall also be taken to include any collection of machines that individually or jointly execute instructions 124 to perform any one or more of the methodologies discussed herein.

The example computer system 400 includes a processor 402 (e.g., a central processing unit (CPU), a graphics processing unit (GPU), a digital signal processor (DSP), one or more application specific integrated circuits (ASICs), one or more radio-frequency integrated circuits (RFICs), or any combination of these), a main memory 404, and a static memory 406, which are configured to communicate with each other via a bus 408. The computer system 400 may further include visual display interface 410. The visual interface may include a software driver that enables displaying user interfaces on a screen (or display). The visual interface may display user interfaces directly (e.g., on the screen) or indirectly on a surface, window, or the like (e.g., via a visual projection unit). For ease of discussion the visual interface may be described as a screen. The visual interface 410 may include or may interface with a touch enabled screen. The computer system 400 may also include alphanumeric input device 412 (e.g., a keyboard or touch screen keyboard), a cursor control device 414 (e.g., a mouse, a trackball, a joystick, a motion sensor, or other pointing instrument), a storage unit 416, a signal generation device 418 (e.g., a speaker), and a network interface device 420, which also are configured to communicate via the bus 408.

The storage unit 416 includes a machine-readable medium 422 on which is stored instructions 424 (e.g., software) embodying any one or more of the methodologies or functions described herein. The instructions 424 (e.g., software) may also reside, completely or at least partially, within the main memory 404 or within the processor 402 (e.g., within a processor's cache memory) during execution thereof by the computer system 400, the main memory 404 and the processor 402 also constituting machine-readable media. The instructions 424 (e.g., software) may be transmitted or received over a network 426 via the network interface device 420.

While machine-readable medium 422 is shown in an example embodiment to be a single medium, the term "machine-readable medium" should be taken to include a single medium or multiple media (e.g., a centralized or distributed database, or associated caches and servers) able to store instructions (e.g., instructions 424). The term "machine-readable medium" shall also be taken to include any medium that is capable of storing instructions (e.g., instructions 424) for execution by the machine and that cause the machine to perform any one or more of the methodologies disclosed herein. The term "machine-readable medium" includes, but not be limited to, data repositories in the form of solid-state memories, optical media, and magnetic media.

Figure 5:
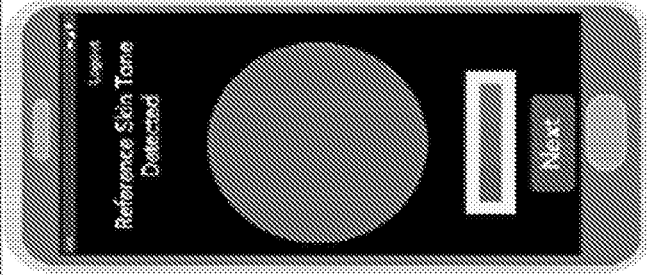
FIG. 5 depicts exemplary images showing a base skin tone image and a skin concern image, in accordance with one embodiment.
Figure 5:
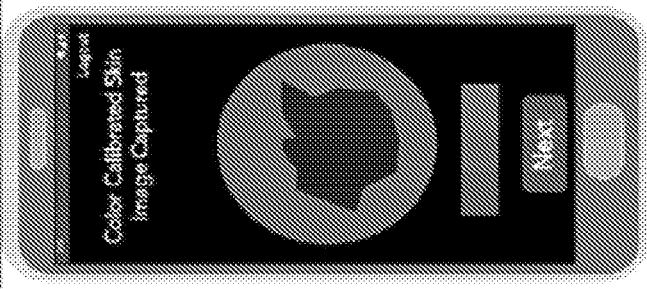

FIG. 5 depicts exemplary images showing a base skin tone image and a skin concern image, in accordance with one embodiment. Base skin tone image 510 is shown being captured by an operator, who as depicted, is not the patient. The imaging device used is shown to be a smartphone camera. The imaging device is shown to display the reference skin tone of the patient.

Skin concern image 520 is shown being captured by the operator. Skin concern image 520 includes an image of a mole. Skin concern image 520 is calibrated using an adapted reference profile, which results in a skin concern image that, when input into a classifier for diagnosis, optimizes the accuracy of the results of the diagnosis.

Figure 6:
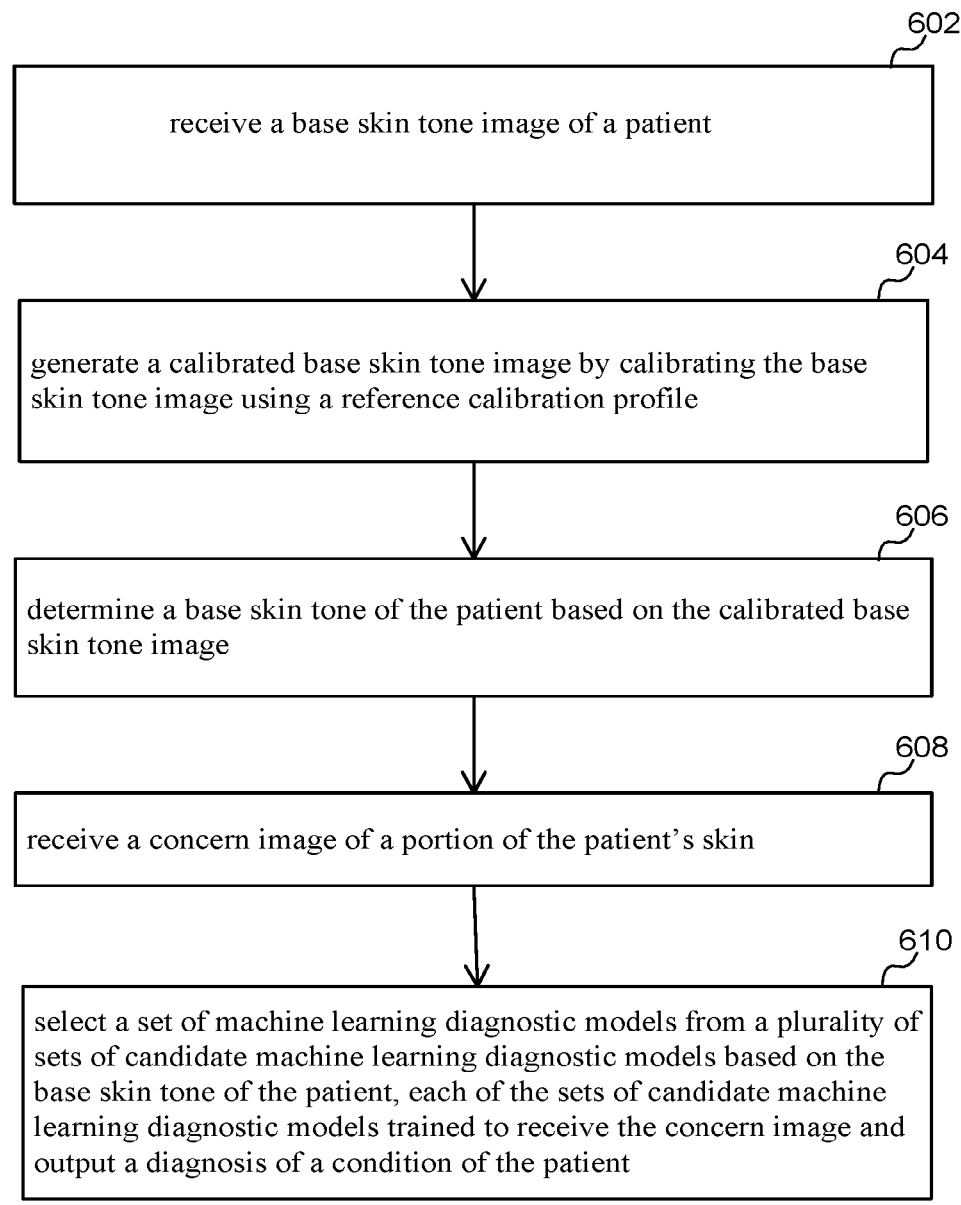
FIG. 6 depicts an exemplary flow chart for determining a diagnosis based on a base skin tone of a patient, in accordance with one embodiment.

FIG. 6 depicts an exemplary flow chart for determining a diagnosis based on a base skin tone of a patient, in accordance with one embodiment. Process 600 may begin with skin image calibration tool 130 receiving 602 a base skin tone image of a patient. The base skin tone image may be received by image capture module 210, which may be executed by processor 402. The base skin tone image may be base skin tone image 510. Skin image calibration tool 130 generates 604 a calibrated skin tone image (e.g., using image capture module 210) by calibrating the base skin tone image using a reference calibration profile (e.g., as retrieved from reference calibration profile database 250).

Skin image calibration tool 130 determines 606 a base skin tone of the patient based on the calibrated base skin tone image (e.g., using base skin tone determination module 220). Care selection tool 140 receives 608 a concern image of a portion of the patient's skin (e.g., as depicted in concern image 520). Care selection tool 140 selects 610 (e.g., using classifier selection module 330) a set of machine learning diagnostic models from a plurality of sets of candidate machine learning diagnostic modules based on the base skin tone of the patient, each of the sets of candidate machine learning models trained to receive the concern image and output a diagnosis of a condition of the patient.

Summary

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method for determining a diagnosis based on a base skin tone of a patient, the method comprising:
   receiving a base skin tone image of a patient;
   generating a calibrated base skin tone image by calibrating the base skin tone image using a reference calibration profile;
   determining a base skin tone of the patient based on the calibrated base skin tone image;
   receiving a concern image of a portion of the patient's skin;
   selecting a set of machine learning diagnostic models from a plurality of sets of candidate machine learning diagnostic models based on the base skin tone of the patient, each of the sets of candidate machine learning diagnostic models trained to receive the concern image and output a diagnosis of a condition of the patient;
   inputting the base skin tone and the concern image into at least one classifier of the selected set of machine learning diagnostic models; and
   receiving, as output from the at least one classifier, information from which the diagnosis is derived.

2. The method of claim 1, wherein generating the calibrated skin tone image is performed responsive to determining that the base skin tone image satisfies a quality criterion.

3. The method of claim 1, wherein determining the base skin tone of the patient based on the calibrated image comprises:
   determining a numerical representation of each pixel of the calibrated base skin tone image;
   generating an aggregate representation by performing a statistical operation based on each numerical representation;
   identifying a point in a color space corresponding to the aggregate representation; and
   mapping the point in the color space into a discrete value in a classification system.

4. The method of claim 1, wherein the method further comprises generating a plurality of calibrated base skin tone images, the plurality comprising the calibrated base skin tone image, and wherein determining the base skin tone of the patient based on the calibrated image further comprises:
   inputting each of the plurality of calibrated base skin tone images into a measurement classifier; and
   receiving as output from the measurement classifier the base skin tone.

5. The method of claim 1, wherein the method further comprises:
   generating an adapted imaging profile based on the reference calibration profile and the base skin tone; and
   calibrating the concern image using the adapted imaging profile.

6. The method of claim 1, wherein the method further comprises determining a classification that corresponds to the base skin tone, wherein selecting the set of machine learning diagnostic models comprises selecting a diagnosis classifier that corresponds to the classification, and wherein the method further comprises:
   inputting the concern image into the selected diagnosis classifier; and
   receiving, as output from the selected diagnosis classifier, information from which the diagnosis is derived.

7. The method of claim 1, wherein determining the method further comprises:
   inputting the concern image into at least one classifier of the selected set of machine learning diagnostic models;
   receiving, as output from the at least one classifier, information from which the diagnosis is derived;
   modifying the information based on the base skin tone; and
   determining the diagnosis based on the modified information.

8. The method of claim 1, wherein the method further comprises:
   determining whether the concern image is diagnosable based on the base skin tone; and
   responsive to determining that the concern image is not diagnosable, outputting an indication that the concern image is not diagnosable.

9. The method of claim 1, wherein the diagnosis of the condition comprises a probability that the patient has the condition.

10. A computer program product for determining a diagnosis based on a base skin tone of a patient, the computer program product comprising a non-transitory computer-readable storage medium containing computer program code for:
    receiving a base skin tone image of a patient;

generating a calibrated base skin tone image by calibrating the base skin tone image using a reference calibration profile;

determining a base skin tone of the patient based on the calibrated base skin tone image;

receiving a concern image of a portion of the patient's skin;

selecting a set of machine learning diagnostic models from a plurality of sets of candidate machine learning diagnostic models based on the base skin tone of the patient, each of the sets of candidate machine learning diagnostic models trained to receive the concern image and output a diagnosis of a condition of the patient;

inputting the base skin tone and the concern image into at least one classifier of the selected set of machine learning diagnostic models; and receiving, as output from the at least one classifier, information from which the diagnosis is derived.

11. The computer program product of claim 10, wherein generating the calibrated skin tone image is performed responsive to determining that the base skin tone image satisfies a quality criterion.

12. The computer program product of claim 10, wherein determining the base skin tone of the patient based on the calibrated image comprises:

determining a numerical representation of each pixel of the calibrated base skin tone image;

generating an aggregate representation by performing a statistical operation based on each numerical representation;

identifying a point in a color space corresponding to the aggregate representation; and mapping the point in the color space into a discrete value in a classification system.

13. The computer program product of claim 10, wherein the computer code is further for generating a plurality of calibrated base skin tone images, the plurality comprising the calibrated base skin tone image, and wherein determining the base skin tone of the patient based on the calibrated image further comprises:

inputting each of the plurality of calibrated base skin tone images into a measurement classifier; and receiving as output from the measurement classifier the base skin tone.

14. The computer program product of claim 10, wherein the computer code is further for determining a classification that corresponds to the base skin tone, wherein selecting the set of machine learning diagnostic models comprises selecting a diagnosis classifier that corresponds to the classification, and wherein the computer code is further for:

inputting the concern image into the selected diagnosis classifier; and receiving, as output from the selected diagnosis classifier, information from which the diagnosis is derived.

15. The computer program product of claim 10, wherein the computer code is further for:

inputting the concern image into at least one classifier of the selected set of machine learning diagnostic models;

receiving, as output from the at least one classifier, information from which the diagnosis is derived;

modifying the information based on the base skin tone; and determining the diagnosis based on the modified information.

16. The computer program product of claim 10, wherein the diagnosis of the condition comprises a probability that the patient has the condition.

17. A method for determining a diagnosis of a patient, the method comprising:

receiving biometric data of at least a portion of a patient;

inputting the biometric data into a classifier trained to obtain an attribute of the patient;

receiving, as output from the classifier, the attribute of the patient; and selecting a set of machine learning diagnostic models from a plurality of sets of candidate machine learning diagnostic models based on the attribute of the patient, each of the sets of candidate machine learning diagnostic models trained to receive the attribute and output a diagnosis of a condition of the patient, wherein each of the sets of candidate machine learning diagnostic models are trained to receive a concern image depicting an organ of the patient in addition to the attribute, and to output the diagnosis of the condition of the patient based on both the attribute and the concern image.

* * * * *